United States Patent [19]
Iff

[11] Patent Number: 5,146,792
[45] Date of Patent: Sep. 15, 1992

[54] SAMPLING DEVICE WITH A VALE UNIT AND A RECEIVING UNIT

[75] Inventor: René Iff, Lostorf, Switzerland

[73] Assignee: Neotech AG, Hombrechtikon, Switzerland

[21] Appl. No.: 638,608

[22] Filed: Jan. 7, 1991

[30] Foreign Application Priority Data

Jan. 30, 1990 [CH] Switzerland ............ 285/90

[51] Int. Cl.$^5$ ............................................. G01N 1/00
[52] U.S. Cl. .................................. 73/863.86; 251/339
[58] Field of Search ................. 73/863.86; 251/321, 251/322, 339, 354

[56] References Cited

U.S. PATENT DOCUMENTS

| | | | |
|---|---|---|---|
| 2,370,260 | 2/1945 | Robison | 73/863.86 |
| 2,623,544 | 12/1952 | Waters et al. | 73/863.86 |
| 2,875,976 | 3/1959 | Harwood | 251/321 |
| 4,934,201 | 6/1990 | Grimminger et al. | 73/863.11 |

FOREIGN PATENT DOCUMENTS 2071846 9/1981 United Kingdom ............ 73/863.86

*Primary Examiner*—Robert Raevis
*Attorney, Agent, or Firm*—Egli International

[57] ABSTRACT

The receiving unit can be removed from the valve unit and fastened preferentially by means of a fast locking means, in particular of a bayonet lock, a thread or a plug-in lock. The valve unit is spring-biased in the closing direction and opens toward the inside. The receiving unit is spring-biased in the closing direction and opens toward the outside. The valve unit and receiving unit are linked in sealing connection preferentially by means of mating ball joints. At the valve unit a discharge bore hole may lead from the discharge opening toward the outside the valve bar being located outside the discharge bore hole. At the lock the closure bar may extend outward from the opening of the receiving unit. The actuating device acts on the lock of the receiving unit preferentially by a two-part driver device with a cam coupled to the closure housing and a recess arranged at the closure bar. A locking device preferentially permits the opening of the closure only if the receiving unit is arranged at the valve unit and locked in a predetermined actuating position in relation to it.

12 Claims, 4 Drawing Sheets

SAMPLING DEVICE WITH A VALE UNIT AND A RECEIVING UNIT

BACKGROUND OF THE INVENTION

1. Field of the Invention

The invention relates to a sampling device provided with a valve unit to be arranged at a conduit and a receiving unit arranged in a removable way for receiving a sample of a fluid flowing in the conduit, the valve unit being spring-biased in the closing direction, the receiving unit being equipped with a closure that is spring-biased in the closing direction, the valve unit being constructed to open towards the inside and the receiving unit to open towards the outside, and the receiving unit when arranged at the valve unit being effectively connected with the lock in a sealing way.

2. Description of the Prior Art

For various reasons (quality control, process monitoring, environmental protection, etc.), there are a growing number of instances where the removing of liquid or gaseous samples from conduits is required. The samples range from innocuous products such as water (e.g. reprocessing) and beverages to fuels and pure cold solvents and to all sorts of dangerous chemicals (hot acids, halogens, etc.).

Harmless substances may be tapped from the conduit by customary means such as by way of a faucet or a valve. However, the resulting dead space or the short dead-end conduit are very disadvantageous because a certain amount of the substance to be tapped needs to be poured away and/or more of the substance than the required amount needs to be tapped in order to obtain a significant sample. Besides, the dripping fluid requires subsequent rinsing and/or cleaning.

The more poisonous, dangerous and/or expensive a product, the more important becomes the problem of sampling. In devices for the removing of such liquid or gaseous samples from conduits, for example in installations of the chemical industry or the foodstuffs and beverages industry, it must guaranteed that samples are tapped from conduits and filled in receptacles in a way that neither the contents of the conduit nor the sample get into contact with the ambient air or with any alien matter such as precipitation or residues from an earlier sampling process, and that also after the removal of the receptacle no product will escape as gas into the environment or drip down in the form of a liquid.

From DE-3142875, GB-907495, U.S. Pat. No. 2041694, SU-363890 or FR-2067722 valve units of sampling devices are known which permit the removal of a sample from a conduit and the feeding of it to the connection piece for the connection of a receptacle. Such valve units without an assigned receptacle and with only one connection piece are not capable, on principle, of satisfying the requirements mentioned above.

From DE-929398, U.S. Pat. No. 3744319 and SU-549706 sampling devices are known which enable that a sample be removed from a conduit and that it be fed to a receiving unit. These sampling units possess dead spaces and thus do not satisfy the formulated requirements.

From U.S. Pat. No. 4150575 a sampling device is known which enable that a sample be removed from a conduit and that it be fed to a receptacle of a receiving unit provided with a piston. While this sampling device essentially guarantees that the contents of the conduit or of the sample do not get into contact with the ambient air, and that after the removal of the receiving unit no product will escape and get into the environment, this sampling device is actuated by the mounting or removing process of the receiving unit. The time of the sampling is determined by the actuation of a lock of the receiving unit on the valve body, that is the valve unit is opened during the fastening process of the receiving unit and closed when the tight connection is loosened. If the locking connection of the receiving unit is loosened, which is done manually at the neck of the receiving unit, the receiving unit is released immediately so that it must be held by hand. When handling dangerous products this procedure is inadmissible, work regulations and environmental protection require higher safety standards which are not guaranteed in this case. An actuation of the valve unit independent of the locking of the receiving unit is not provided in this sampling device nor is it possible.

From EP-0141940 a sampling device is known which enables that a sample be removed from a conduit and that it is fed to a receptacle of a receiving unit. This sampling device essentially guarantees that the contents of the conduit or the sample will not get into contact with the ambient air and that after the receiving unit has been removed no product will escape and be set off into the environment. However, the necessary safety is not guaranteed, because the valve unit may also be opened if no receiving unit is arranged at the valve unit. No measures are taken to avoid a possible discharge of products which can escape as gas into the environment or drip down as liquid after the receiving unit has been removed. In the case of this sampling device, an actuation of the valve unit depending on the presence and the locking of the receiving unit is not provided nor is it possible.

SUMMARY OF THE INVENTION

It is the object of this invention to provide a sampling device of the kind mentioned at the outset where the actuation of the valve unit depends on the presence and the connection of the receiving unit, however, not on the time of locking of the receiving unit.

According to the invention, this object is achieved in a sampling device according to claim 1, in that one single actuating device is provided for the simultaneous actuation of the valve unit and the receiving unit, and that this actuating device is effectively connected with the closure head of the receiving unit for the opening of the receiving unit and that it possesses a locking device effectively connected with the valve unit and the receiving unit and adapted to allow an opening of the closure head only if the receiving unit is arranged at the valve unit and in a predetermined actuating position in relation to the valve unit.

Advantageous developments of the sampling device according to the invention result from the relevant claims.

One advantage of the sampling device according to the invention is its simple and safe handling. Valve unit and receiving unit can be coupled easily and without dead spaces by means of fast locking means. Sampling can be performed by one single motion of an actuating lever, valve unit and receiving unit closing automatically if the lever is released. As additional safeguard, coupling and actuation can be mechanically locked with one another so that valve unit and receiving unit can be opened only if the receiving unit sits in the correct position on the valve unit.

BRIEF DESCRIPTION OF THE DRAWINGS

An embodiment example of the invention is described hereinafter in further detail by means of the drawings.

DESCRIPTION OF THE PREFERRED EMBODIMENT

Figure 1:
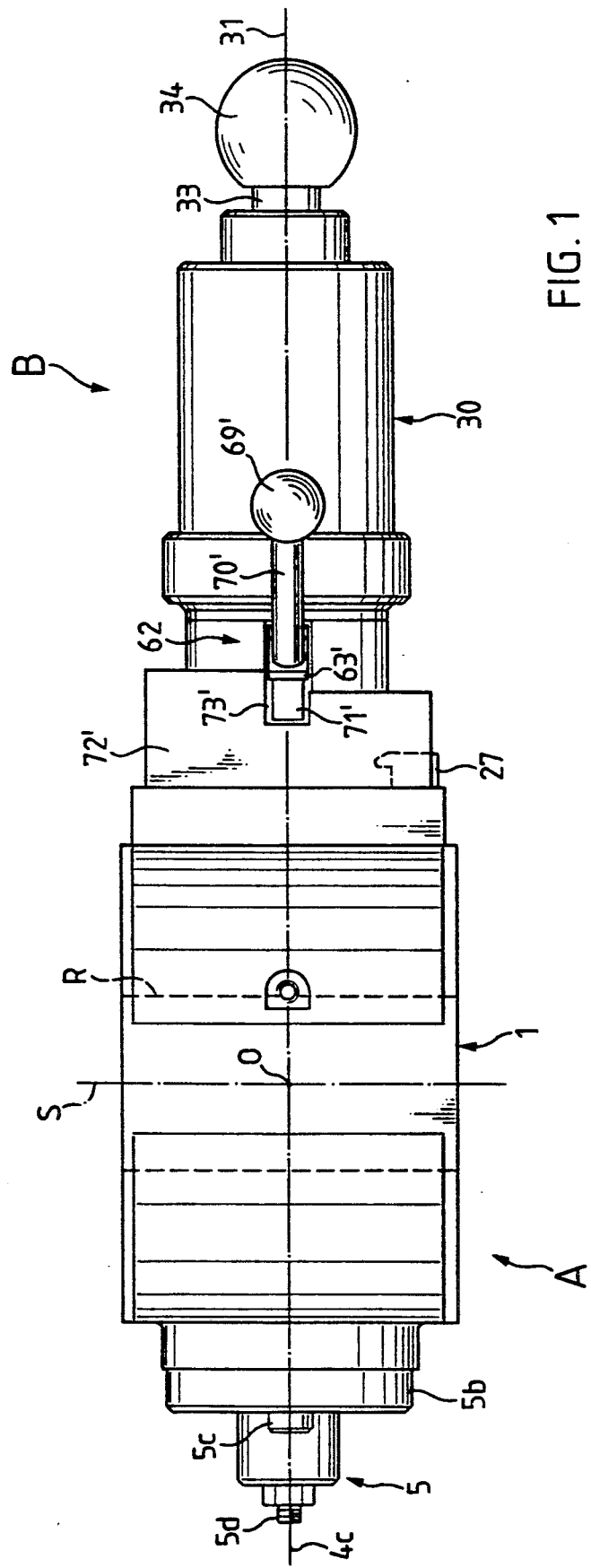
FIG. 1 shows a lateral view of a sampling device according to the invention with a first embodiment of the actuating device.
Figure 2:
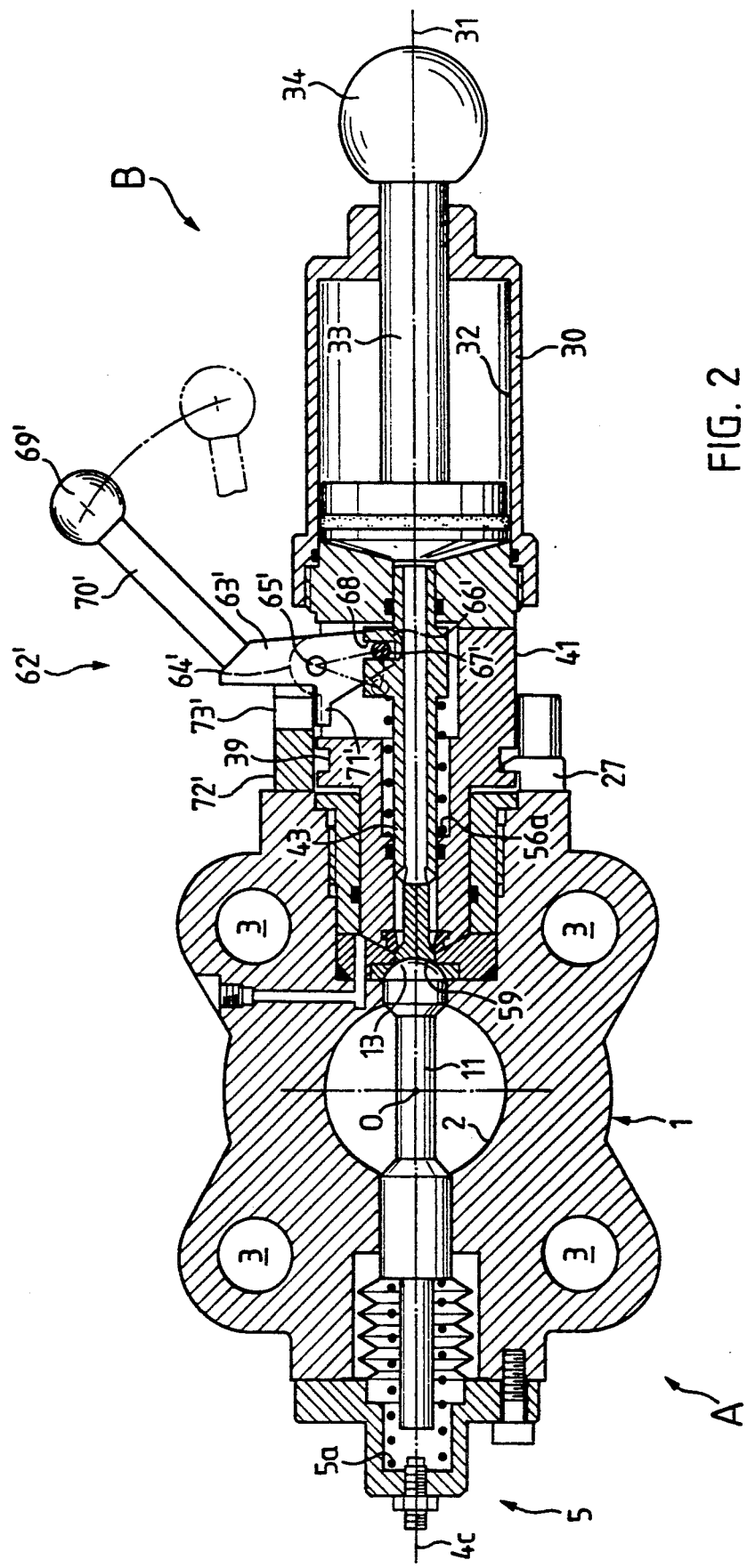
FIG. 2 shows a top view of the sampling device of FIG. 1 with the receiving unit mounted on the valve unit, as section along the line 31 or 4c in FIG. 1.
Figure 3:
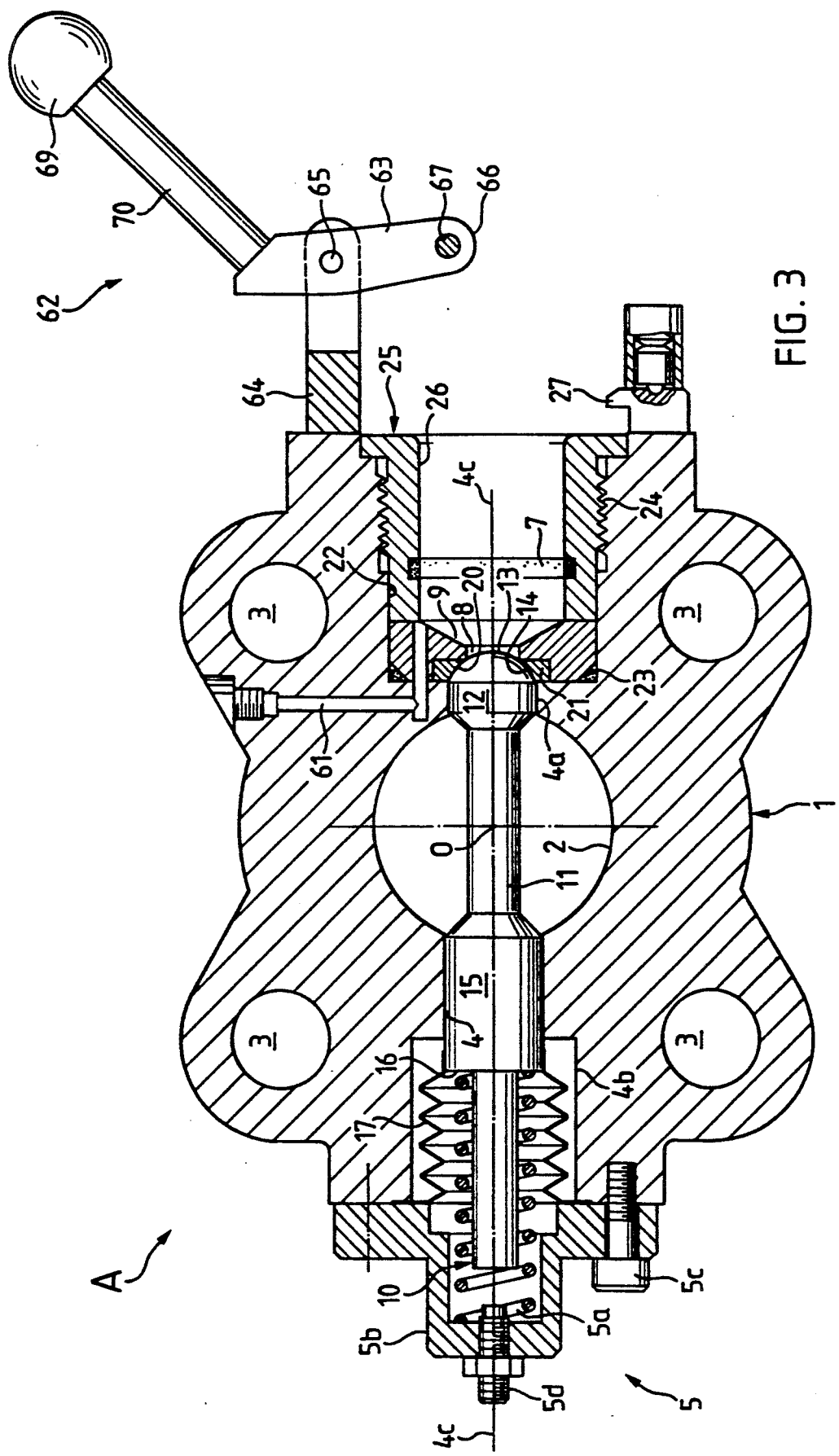
FIG. 3 shows a top view of the valve unit represented in FIG. 2 with a second other embodiment of the actuating device with the receiving unit being removed from the sampling device, also as section along the line 31 or 4c in FIG. 1.

The sampling device represented in FIGS. 1 and 2 includes a valve unit A and a receiving unit B, mounted on top of one another. In FIG. 3 the valve unit A and in FIG. 4 the receiving unit B are shown separately.

The valve unit A is meant to be mounted on a pipe conduit. The receiving unit B is meant to receive a sample from a fluid running in the conduit. The pipe conduit onto which the valve unit A is mounted is implied in FIG. 1 by the dotted lines R and its axis is designated as S. The axis S intersects the plane of FIGS. 2 and 3 in the center O. The receiving unit B is arranged on the valve unit A in the position for receiving the sample and connected to the valve unit A so that it can be detached. Upon the collection of the sample the receiving unit B can be removed from the valve unit A.

The valve unit A (cf. FIGS. 1, 2, and 3) has a valve housing 1 crossed by a bore hole 2 whose interior diameter and direction fit to the pipe conduit R. For the purpose of assembly and fastening of the valve unit A on the pipe conduit R, there are for example four continuous assembly bore holes 3 that are mounted at regular intervals in the outer area of the valve housing 1.

At a right angle to the axis S and diametrically to the bore hole 2 a valve channel 4 is provided whose straight longitudinal axis 4c runs through the center O. Hence, the valve channel 4 crosses the valve housing 1 essentially diametrically in relation to the bore hole 2.

On the one side of the bore hole 2 a part of the valve channel 4 serves as discharge channel 4a for the sampling. At one of its ends the discharge channel 4a runs into the bore hole 2, in the area of its other end it possesses a valve rest 20 for a valve head 12 described at a later instance. The relevant part of the valve channel 4 extends from the valve seat 20 outwards by way of a discharge bore hole 8 up to a discharge opening 9 of the valve unit A.

On the other side of the bore hole 2 a part 4b of the valve channel 4 and the valve housing 1 are constructed for accommodating a closing device 5 of the valve unit A described at a later instance.

In the valve channel 4 an elongated valve bar 11 of a valve body 10 is arranged in a way that it can be moved between two final positions, made possible by the valve bar 11 being supported in the valve channel 4 in a way so that it can be moved in the direction of the longitudinal axis 4c. The valve head 12 is arranged at one end of the valve bar 11 and shaped to fit to the valve bar 11.

In one final position of the valve body 10 the valve head 12 and the valve rest 20 act jointly in a way that the valve head 12 is in contact from the inside with the side of the valve rest 20 facing the center 0. In this closing position of the valve body 10 the connection between the bore hole 2 and the discharge opening 9 for the fluid is interrupted and the valve unit A is therefore closed. For this purpose, the valve head 12 is equipped with an area 13 in the proximity of the valve rest 20, which essentially possesses the shape of a convex ball joint and the valve rest 20 is equipped with an area 14 in the proximity of the valve head 12 which essentially possesses the shape of a concave ball joint or of a truncated cone or yet of a ring so that the two areas 13 and 14 fit together in a sealing connection if they are in contact and pressed onto one another. For even better sealing, the valve rest 20 may for example consist of a sealing material such as silicone or PTFE, whereas the material of the valve unit A may for example be special steel or, if necessary, PTFE-coated metal such as cast steel. Certain parts can also be made of ceramic material, synthetic material or of other non-corrosive materials.

In the other final position of the valve body 10 the valve head is located at a distance from the valve rest 20 toward the inside, in a way that in this opening position of the valve body 10 the fluid may get from the bore hole 2 to the discharge opening 9 and that the valve unit A will thus be opened.

At its end facing away from the valve head 12 the valve body 10 and the closing device 5 of the valve unit A act jointly. This closing device 5 essentially includes a spring element 5a that is arranged essentially in the part 4b of the valve channel 4 between the valve body 10 and a cover 5b. The cover 5b is supported at the valve housing 1 via fastening bolts 5c. If the cover 5b is mounted at the valve housing 1, the spring element 5a is compressed into the direction of the longitudinal axis 4c between the valve body 10 and the cover 5b so that the valve body 10 with the valve bar 11 and the valve head 12 is continuously spring-biased in the direction of the longitudinal axis 4c from the inside toward the discharge opening 9 of the valve unit A. For this purpose, the valve body 10 includes a cylindrical section 15 on its side facing the cover 5b in the area of the valve housing 1, which possesses a greater diameter than the diameter of the valve bar 11 and thus forms a shoulder 16 functioning as stopper for the spring element 5a of the closing device 5 at the valve body 10. In other respects, the cylindrical section 15 serves the purpose of exact guidance of the valve body 10 in the valve channel 4, while a bellows 17 which at one end is connected with the shoulder 16 and at its other end is clamped in between the valve housing 1 and the cover 5b, serves the purpose of sealing the valve body 10 toward the valve housing 1 and toward the outside, as well.

Thus, in FIGS. 2 and 3 the valve unit A is represented in a position, where the connection between the bore hole 2 and the discharge opening 9 for the fluid is interrupted and thus the valve unit A is closed. The valve unit A will then be hermetically sealed and can only be opened by pressing the valve head 12 (for example in a way described at a later instance) against the force of the spring element 5a of the closing device 5 toward the inside.

An adjusting screw 5d permits the adjustment of the final position of the valve body 10 and thus of the distance between the valve head 12 and the valve rest 20 with the valve unit A being open. By means of the adjusting screw 5d the throughput of the fluid from the bore hole 2 toward the discharge opening, with the valve unit A being open as far as possible, may be adjusted.

The valve rest 20 is held in an annular receiving piece 21 which is inserted in a removable way in a location hole 22 that is concentrical in relation to the longitudinal axis 4c and sealed toward the valve housing 1 by means of a gasket 23. The receiving piece 21 is fastened at the valve housing 1 with the help of a sleeve 25 screwed into the location hole 22 at the thread 24. The discharge opening 9 is thus arranged at the receiving piece 21.

As has been mentioned before, the relevant part of the valve channel 4 extends from the valve rest 20 outwards by way of the discharge bore hole 8 up to a discharge opening 9 of the valve unit A. The discharge opening 9 is arranged at a distance from the valve seat 20. The valve bar 11 is located entirely outside the discharge opening 9 and essentially outside the discharge bore hole 8. Thus, the receiving piece 21, the valve rest 20, the discharge bore hole 8 and the discharge opening 9 form an easily replaceable unit, after the sleeve has been unscrewed, whose distance and/or replacement considerably simplifies the maintenance of the valve unit A.

The diameter of the discharge bore hole 8 and of the discharge opening 9 is independent of the diameter of the discharge channel 4a and of the valve head 12 thus permitting to freely select this diameter, for example, for the adaptation of a valve unit A produced in series to different fluids, to the corresponding safety provisions, etc.

The interior face of the sleeve 25 is of cylindrical shape and connected with the receiving piece 21 by way of a corresponding interior face of the receiving piece 21, which is the surface area of a truncated cone. Together the interior faces of the sleeve 25 and of the receiving piece 21 form a hollow pattern destined to receive a matching pattern of a closure housing 41 of the receiving unit B. By replacing the sleeve 25 and the receiving piece 21 a valve unit A produced in series may be adapted to different receiving units B.

The receiving unit B (cf. FIG. 1, 2, and 4) includes first of all a cylindrical receptacle 30 having a shape similar to that of the body of a syringe. The straight longitudinal axis of the receptacle 30 is referred to as 31. In the receptacle 30 a cylindrical cavity 32 for the collection of the fluid sample is provided. In the cavity 32 a plunger 33 similar to the plunger of a syringe is arranged in a way that it can be moved in the direction of the longitudinal axis 31, and it can be actuated manually by way of a knob 34 in order to move a piston 35 along the cavity 32. The piston 35 is sealed in relation to the cylindrical inner face of the cavity 32 by means of a ring gasket 36. The cavity 32 is therefore divided into two parts by the piston 35, into a first part for the collection of the sample and into a second, remaining part which communicates, for example with the ambient air if necessary by way of a filter not represented in this context or which is sealed off, for example, by means of bellows.

Figure 4:
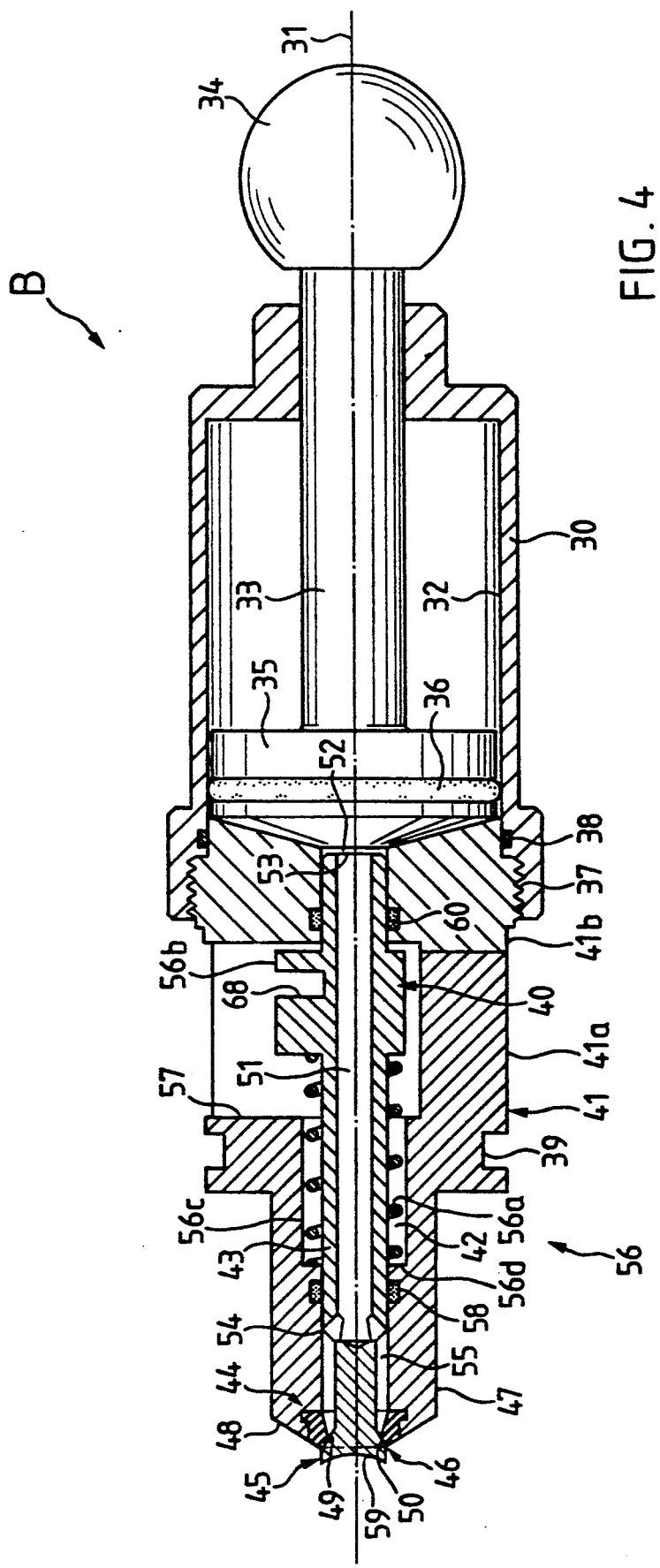
FIG. 4 shows a top view of the receiving unit represented in FIG. 2 with the second embodiment of the actuating device and with the valve unit being removed from the sampling device, also as section along the line 31 or 4c in FIG. 1.

In FIGS. 1, 2, and 4 the plunger 33 is represented in its maximum inserted position in which the part of the cavity 32 destined for the collection of the sample is the smallest, i.e. reduced down to an insignificant dead space.

Furthermore, the receiving unit B (cf. FIGS. 1, 2, and 4) includes the already mentioned closure housing 41 which is screwed onto the receptacle 30 with the help of a thread 37, for example, as represented in FIGS. 2 and 4, and sealed in relation to the cylindrical inner face of the cavity 32 by means of a ring gasket 38 Yet it is also possible to fasten the closure housing 41 with the help of other means onto the receptacle, for example by means of a bayonet lock or similar appliances.

In the closure housing 41 a closure channel 42 is provided which crosses the closure housing 41 in the direction of the longitudinal axis 31 of the receptacle 30. At one of its ends 52 the closure channel 42 runs into the cavity 32, in the vicinity of its other end it possesses a closure rest 44 for a closure head 45 described hereinafter. In the proximity of the closure rest 44 the closure channel 42 extends outward up to an inlet opening 46 of the receiving unit B.

In the proximity of the closure rest 44 the closure housing 41 is equipped with a cylindrical exterior face 47 and an end face 48 in the shape of a truncated cone extending above the closure rest 44 up to the inlet opening 46. Together the exterior face 47 and the end face 48 form a pattern fitting to the interior faces of the sleeve 25 and of the receiving piece 21 of the valve unit A and destined to guarantee accurate positioning and complete sealing of these parts in relation to one another with the respective longitudinal axes 4c and 31 coinciding, when mounting the closure housing 41 of the receiving unit B on the valve housing 1 of the valve unit A.

In the closure channel 42 an elongated closure bar 43 of a closure body 40 is arranged in a way that it may be moved between two final positions, because the closure bar 43 is supported in the closure channel 42 in a way that it may be moved into the direction of the longitudinal axis 31. At one end of the closure bar 43 the already mentioned closure head 45 is arranged and shaped to fit to the closure bar 43. In the proximity of the closure rest 44 an end face 59 of the closure head 45 possesses essentially the shape of a concave ball joint mating exactly with the face 13 of the valve head 12 of the valve unit A, which has been given the shape of a convex ball joint.

In one final position of the closure body 40 the closure head 45 acts jointly with the closure rest 44 in a way that the closure head 45 is in contact from the outside, i.e. at the side of the closure rest 44 not facing the receptacle 30. In this closing position of the closure body 40 the connection between the receptacle 30 and the inlet opening 46 of the receiving unit B for the fluid is interrupted, and the receiving unit B will thus be closed. For this purpose the closure head 45 is provided with an area 49 in the proximity of the closure rest 44 having essentially the shape of a truncated cone or of a spherical segment, and the closure rest 44 is provided with an area 50 in the proximity of the closure head 45 having essentially the shape of a truncated hollow cone or of a concave spherical segment or yet of a ring so that the two areas 49 and 50 fit together in a sealing way if they are in contact and pressed onto one another. For even better sealing the closure rest 44 may, for example, consist of a sealing material such as silicone or PTFE, while the material of the receiving unit B is special steel or, if necessary, PTFE-coated metal such as cast steel. Certain parts may also be made of ceramic material, synthetic material or other non-corrosive materials.

Furthermore, in this closing position of the closure body 40 the other end 53 of the closure bar 43 is located essentially at the end 52 of the closure channel 42 where it runs into the cavity 32. In this closing position of the closure body 40 the closure bar 43 essentially extends not only over the whole length of the closure channel 42, but in the vicinity of the closure head 45 it still reaches through the encompassing inlet opening 46 of the receiving unit B and even further.

In the other final position of the closure body 40, the closure head 45 is located at a distance from the closure rest 40 toward the outside, in a way that in the opening position of the closure body 40 the fluid may get into the cavity 32 of the receptacle 30 by way of the inlet opening 46, and the receiving unit B will thus be open. For this purpose the closure body 40 is equipped with an axial longitudinal bore hole 51 extending from the end 53 of the closure bar 43 up to a spot 54 shortly before the closure head 45. In this spot 54, bore holes located diagonally to the longitudinal axis 31 create a link between the longitudinal bore hole 51 and a cavity 55 encompassing the closure head 45 in the closure channel 42 and coaxially to it from the spot 54 up to the inlet opening 46.

In the area of the longitudinal bore hole 51 the closure body 10 acts jointly with a closing device 56 of the receiving unit B. This closing device 56 essentially includes a spring element 56a arranged essentially in the closure channel 42 between the closure body 40 and the closure housing 41. The spring element 56a is compressed in the direction of the longitudinal axis 31 between the closure body 40 and the closure housing 41 so that the closure body 40 with the closure bar 43 and the closure head 45 is constantly spring-biased in the direction of the longitudinal axis 31 from the outside toward the inlet opening 46 of the receiving unit B. For this purpose, the closure body 40 includes a block 56b in its central area arranged in a suitable recess 57 of the closure housing 41 in a movable way whose side facing the closure head 45 forms a stopper for the spring element 56a. The recess leads from the closure channel 42 essentially radially outwards in relation to the longitudinal axis. At the closure channel 42 a cylindrical section 56c is provided extending from the recess 57 until shortly before the spot 54 and having a greater diameter than the diameter of the closure bar 43. For this reason, this cylindrical section 56c forms a shoulder 56d at its end closer to the closure rest 44 functioning as stopper for the spring element 56a of the closing device 56 at the closure housing 41.

In order to facilitate the mounting process, in particular of the closure body 40 and of the spring element 56a in the closure housing 41, it is for example constructed as having two parts 41a and 41b. The two parts 41a and 41b are mounted on one another by means of (not represented) screws, yet they may also be fastened on one another in another way, for example they can be screwed on.

The cylindrical section of the closure channel 42 located between the closure rest 44 and the shoulder 56d serves for the exact guidance of the closure body 40 in the closure channel 42, this section of the closure channel 42 being sealed by means of a ring gasket 58. A fluid entering the cavity 55 through the inlet opening 46 may thus not advance to section 56c of the closure channel 42 and from there get to the outside by way of the recess 57. Besides, the closure body 40 is sealed by means of a ring gasket 60 near the end 52 of the closure channel 42 in relation to a cylindrical end zone of the closure bar 43, the fluid may thus get from the cavity 55 merely to the bore hole 51 and from there only to the end 53 of the closure bar 43 and then, in accordance with the return of the piston 35, get to the cavity 32 of the receptacle 30.

For this reason, the receiving unit B in FIG. 4 is represented in a position where the connection between the inlet opening 46 and the cavity 32 of the receptacle 30 for the fluid is interrupted and the receiving unit B is therefore closed. The receiving unit B will then be hermetically sealed and may only be opened by pressing (for example in the way described at a later instance) the closure body 40 against the force of the spring element 56a of the closing device 56 towards the outside.

The receiving unit B can be mounted at the valve unit A by means of a fast locking means. In the embodiment represented, this fast locking means is a bayonet lock in which a cam 27 of the valve unit A acts jointly with a groove 39 of the receiving unit B, but will not be fully engaged until the receiving unit B arrives at a predetermined rotating position in relation to the valve unit A which is the final position of the rotation of the bayonet lock. If the receiving unit B is fastened at the valve unit A, for example by means of the represented fast locking means, a ring gasket 7 serves the purpose of sealing between the exterior face 47 of the closure housing 41 of the receiving unit B and the cylindrical interior face 26 of the sleeve 25 of the valve unit A. Besides, additional sealing may be done by pressing the closure rest 44 of the receiving unit B onto the receiving piece 21 of the valve unit A (in the proximity of the essentially coinciding inlet opening 46 of the receiving unit B and discharge opening 9 of the valve unit A).

A similar result not represented in the drawing may be achieved by means of a thread or a plug-in lock instead of a bayonet lock, as long as the final position of the rotation required by the thread or of the insert motion required by the plug-in lock is defined with sufficient accuracy for reasons that are explained at a later instance.

If the receiving unit B is fastened at the valve unit A the end face 59 of the closure head 45 of the receiving unit B and the area 13 of the valve head 12 of the valve unit A will be in a perfectly mating contact. Thus no significant dead space remains between the receiving unit B and the valve unit A whose contents might mix with the sample and falsify it. If necessary, such a dead space can be vented via the channel 61 leading to the outside from this dead space through the receiving piece 21 and the closure housing 41 rinsed with protective gas or even put under vacuum, in particular during the insertion of the receiving unit B into the valve unit A.

For the sampling process, the device according to the invention is actuated by means of a single actuating device 62 for the simultaneous opening of the valve unit A and the receiving unit B. This actuating device 62 includes a two-part driver device. One part of the driver device is effectively connected with the valve housing 1, the other part of the driver device is effectively connected with the closure bar 43. However, actuation of the driver device is—as is hereinafter explained—possible only if the receiving unit B is fastened at the valve unit A in its final position.

In a variant of the actuating device 62 represented in FIGS. 3 and 4 one part of the driver device includes essentially an elongated lever 63 which approximately in its center is coupled to the a carrier element 64 provided at the valve housing 1 by means of a spigot 65. The lever 63, the carrier element 64 and the spigot 65 are dimensioned and arranged in a way that the swiveling axis of the lever 63 runs essentially at a right angle to the longitudinal axis 4c in the spigot 65 and the swiveling plane of the lever 63 essentially at a right angle to the axis S of the pipe conduit R and that one end 66 of the lever 63 may be inserted into the recess 57 of the closure housing 41 of the receiving unit B if it is fastened at the valve unit A in its final position.

In the proximity of its end 66 an approximately cylindrical cam 67 is arranged at the lever 63 whose axis runs also essentially at a right angle to the longitudinal axis 4c. The cam 67 is dimensioned in a way and arranged at the lever 63 that it may be inserted into a recess 68 of the block 56b of the receiving unit B, if it is fastened at the valve unit A in its final position and the end 66 of the lever 63 is inserted into the recess 57 of the receiving unit B.

The lever 63 and its cam 67 can be actuated manually by means of a handle 70 provided with a knob 69. Yet it is understandable that also known motor-driven, in particular hydraulic or pneumatic embodiments can be used for the actuation of the lever 63.

The other part of the driver device consists essentially of the already mentioned recess 68 of the block 56b of the receiving unit B.

It can be recognized that the lever 63 or the cam 67 of the valve unit A can only be inserted into the recess 57 of the closure housing 41 or the recess 68 of the block 56b of the receiving unit B if the closure housing 41 is correctly mounted in relation to the valve housing 1, that is not twisted or displaced. It can also be recognized that the closure housing 41 may only be moved, that is twisted or displaced, in relation to the valve housing 1 if the lever 63 or the cam 67 of the valve unit A has been unscrewed from the recess 57 of the closure housing 41 or from the recess 68 of the block 56b of the receiving unit B. Thus the two-part driver device simultaneously forms a two-part locking device for the receiving unit B onto the valve unit A which permit an opening of the closure only if the receiving unit is arranged at the valve unit and is located in the predetermined actuating position in relation to the valve unit.

In another embodiment of the actuating device 62' represented in FIG. 2 one part of the driver device includes an elongated lever 63' coupled approximately in its center to a carrier element 64' provided at the closure housing 41 by means of a spigot 65' The lever 63', the carrier element 64' and the spigot 65' are dimensioned and arranged in a way that the swiveling axis of the lever 63' runs essentially at a right angle to the longitudinal axis 31 in the spigot 65 and that one end 66' of the lever 63' may be inserted into the recess 57 of the closure housing 41.

In the proximity of its end 66' an approximately cylindrical cam 67' is arranged at the lever 63' whose axis runs also essentially at a right angle to the longitudinal axis 31. The cam 67' is dimensioned in a way and arranged at the lever 63' that it may be inserted into a recess 68 of the block 56b, if the end 66' of the lever 63' is inserted into the recess 57.

The lever 63' and its cam 67' can be actuated manually by means of a handle 70' provided with a knob 69' Yet also in this case it is understandable that also known motor-driven, in particular hydraulic or pneumatic embodiments can be used for the actuation of the lever 63'.

Furthermore, this part of the driver device consists essentially of the already mentioned recess 68 of the block 56b of the receiving unit B.

It can be recognized that the lever 63' of the cam 67' can always be inserted into the recess 57 of the lock housing 41 or the recess 68 of the block 56b of the receiving unit B while this part of the driver device is not in any way connected with the valve unit A. Therefore, this part of the driver device is only effectively connected with the lock bar 43.

The other part of the driver device effectively connected with the valve housing 1 consists essentially of the fast locking means by means of which the receiving unit B can be fastened at the valve unit A.

Hence, in this embodiment represented in FIG. 2 the two-part driver device does not constitute per se a locking device for the receiving unit B onto the valve unit A, which would not permit an opening of the closure until the receiving unit is arranged at the valve unit and is located in the predetermined actuating position in relation to the valve unit. For achieving this locking function a special locking device is provided in the embodiment of the actuating device 62' represented in FIG. 2, having a two-part construction with one part being arranged at the valve housing and another part at the closure housing.

The part of the locking device arranged at the lock housing includes a cam 71' arranged at the lever 63, while the part of the locking device arranged at the locking device includes a web 72' arranged on the valve housing 1 in rigid way and a recess 73' located inside of it. The cam 71', the web 72' and the recess 73' are dimensioned and arranged in a way that the cam 71' may only be inserted into the recess 73' by moving the lever 63' if the closure housing 41 has been correctly inserted in relation to the valve housing 1, that is neither twisted nor displaced.

It can be recognized that the closure housing 41 may only be moved, that is twisted or displaced, in relation to the valve housing 1 if the lever 63' or the cam 67' of the receiving unit B has been unscrewed from the recess 73' of the valve unit A. Thus the two-part driver device guarantees that an opening of the closure will only be permitted if the receiving unit is arranged at the valve unit and is located in the predetermined actuating position in relation to the valve unit.

In all previously described embodiments the sampling device is employed in the following way. Let us assume that in the initial position the valve unit A is mounted on the pipe conduit R and the receiving unit B is provided separately, that is separately from the valve unit A. If necessary, the cavity 32 of the receptacle 30 in the receiving unit B will be rinsed with protective gas or protective liquid and the piston 35 with the plunger 33 and the knob 34 has been inserted up to the end 52 of the lock channel 42. Now, the receiving unit B is inserted into the valve unit A and fastened or locked by means of the fast locking means. After the final position (rotating position or plug-in position) of the receiving unit B at the valve unit A has been reached the knob 69 or 69' and the handle 70 or 70' may be moved in a way that the cam 67 or 67' will engage with the recess 68 of the block 56b and act jointly with it in order to push the closure body 40 of the receiving unit B against the force of the spring element 56a toward the valve unit A. Since the closure head 45 of the receiving unit B and the valve head 12 of the valve unit A fit together exactly and are in contact, the displacement of the closure body 40 of the receiving unit B causes the corresponding displacement of the valve body 10 of the valve unit A against the force of the spring element 5a. The receiving unit B and the valve unit A are therefore opened simultaneously thus permitting that the fluid in the pipe conduit R gets to the cavity 32 of the receptacle 30 and the sample will thus be filled into the cavity 32 of the receptacle.

If the knob 69 or 69' and the handle 70 or 70' is released the force of the spring elements 5a and 56a causes that the receiving unit B and the valve unit A are closed. It is only after this closing process that the locking device will permit the removal of the receiving unit B from the valve unit A. Since there is no significant dead space between the receiving unit B and the valve unit A, no significant amount of the possibly dangerous fluid is set free, undesired liquids cannot drip down, and undesired gases cannot escape into the air. The sample is filled into the cavity 32 of the receptacle 30 and sealed in, it may be transported in and together with the receiving unit B to locations of further use (analysis, for example).

In the first embodiment of the actuating device 62 represented in FIGS. 3 and 4 the receiving unit B may not be opened at all without the use of a special means: that is why this embodiment is the safer one with regard to the handling of a receptacle filled with a fluid, besides, not every receiving unit requires a wholly separate actuating device, which on the whole is less costly if a great number of receiving units are to be provided for each valve unit. For the removal and the use (e.g. for analysis) of the fluid sample filled into the receptacle 30, a special device will be necessary having the same parts of the driver device and the locking device as the valve unit.

In the second embodiment represented in FIG. 2 of the actuating device 62 the receiving unit B can be opened at any time: that is why this embodiment is more practical with regard to the handling of a receptacle filled with a fluid, yet the receiving units are quite more costly because of the separate actuating device.

In general, the embodiment of the invention is in no way whatsoever limited to the herein described development that was specified only as example. Many equivalent developments are known to the expert whose embodiment does not leave the scope of this invention. From among the equivalent developments such developments are named that can be realized with opposite opening directions of the valve unit (A) and the receiving unit (B), with other types of faces than the described combination of ball joints and/or with other kinds of couplings than the combinations of cams and recesses. The described, manually controlled actuating device can also be replaced by an equivalent motor-driven actuating device.

I claim:

1. A sampling device having a valve unit arranged at a conduit and a receiving unit arranged in a removable manner at said valve unit for receiving a sample of a fluid flowing in said conduit and in a bore hole of said valve unit, said valve unit having a valve head that is spring biased in a closing direction of said valve unit, said receiving unit having a closure head that is spring-biased in a closing direction of said receiving unit, said valve unit being constructed to be opened by actuation of said valve head is a direction which is opposed to the closing direction and directed towards said bore hole of said valve unit, and said receiving unit being constructed to be opened by actuation of said closure head in a direction which is opposed to the closing direction of said receiving unit and directed towards the bore hole of said valve unit when the receiving unit is arranged at said valve unit, and the receiving unit when arranged at the valve unit being effectively connected therewith in a sealing manner, said sampling device comprising a single actuating device for the simultaneous actuation of said valve unit and said receiving unit, said actuating device being effectively connected with said closure head of said receiving unit for opening said receiving unit and having a locking device effectively connected with said valve unit and said receiving unit and adopted to allow an opening of said closure head of said receiving unit only if said receiving unit is arranged at said valve unit in a predetermined actuating position.

2. The sampling device according to claim 1, wherein said receiving unit is fastened to said valve unit by means of a fast locking means and that the actuating position is a final position of said receiving unit in relation to the valve unit determined by said fast locking means.

3. The sampling device according to claim 2, wherein said fast locking means is a bayonet lock or a thread and the actuating position is a final position of a rotation of said receiving unit in relation to said valve unit determined by said bayonet lock or thread.

4. The sampling device according to claim 2, wherein said fast locking means is a plug-in lock and the actuating position is a final position of said receiving unit in relation to said valve unit determined by said plug-in lock.

5. The sampling device according to claim 1, wherein said valve unit comprises:
   (a) a valve housing comprising:
      a bore hole fitting to an interior diameter of said conduit,
      a valve channel crossing said valve housing in a straight and essentially diametrical way in relation to said bore hole in the direction of a longitudinal axis of said valve channel,
      a discharge channel formed by a part of said valve channel located on one side of said bore hole, running into the bore hole at one of its ends and having a valve rest in the range of its other end, said valve rest facing substantially towards said bore hole of said valve unit, and
      a discharge opening for said valve unit at the end of the valve channel in the proximity of said valve rest, and
   (b) a valve body arranged in said valve channel between two final positions in a movable way and comprising:
      an elongated valve bar received in said valve channel in a movable way,
      a valve head arranged and formed at one end of said valve bar, being in contact with said valve rest in the one final position, and being at a distance from said valve rest towards said bore hole of said valve unit in the other final position,
      said valve bar being supported at said valve housing at its end facing away from said valve head by way of a closing device of said valve unit and constantly spring-biased by said closing device in the direction of the longitudinal axis of said valve channel from the inside toward the discharge opening of said valve unit.

6. The sampling device according to claim 5, wherein said receiving unit comprises:
   (a) a receptacle having a cavity for receiving the sample,
   (b) a closure housing comprising:
      a closure channel crossing said closure housing in a straight manner in the direction of a longitudinal axis of said closure channel, said closure channel running into the cavity at one of its ends and being equipped with a closure rest in proximity to its other end, said closure rest facing substantially towards said bore hole of said valve unit when said receiving unit is arranged at said valve unit, and an inlet opening of said receiving unit at the end of said closure channel in proximity to said closure rest, and
   (c) a closure body arranged in said closure channel between two final positions in a movable manner and comprising:
      an elongated closure bar received in said closure channel in a movable manner, and
      a closure head arranged at the one end of said closure bar, said closure head being in contact with said closure rest in the one final position and being at a distance from said valve rests towards said bore hole of said valve unit when said receiving unit is arranged at said valve unit in the other final position, said closure bar being supported at said closure housing at its end facing away from said closure head by means of a closing device of the receiving unit and constantly spring-biased by said closing device in the direction of the longitudinal axis of said closure channel from the outside toward the inlet opening of said receiving unit,
   the longitudinal axis of said valve channel and the longitudinal axis of said closure channel are in coincidence when said receiving unit is arranged at said valve unit,
   said valve head in the proximity of said valve rest and said closure head in the proximity of said closure rest being provided with the corresponding areas which are in mating contact with the receiving unit is arranged at said valve unit, the discharge opening of said valve unit is positioned at a distance from the valve rest and linked to it in a discharge bore hole, said valve bar being positioned essentially outside said discharge bore hole and the discharge opening, the inlet opening of said receiving unit is located essentially in the proximity of said closure rest, said closure bar being enclosed by the inlet opening and extending from said receiving unit above the inlet opening.

7. The sampling device according to claim 6, wherein said area of said valve head is constructed as a convex ball joint and said area of said closure head as a concave ball joint.

8. The sampling device according to claim 6, wherein said actuating device includes a two-part driver device, a first part of said driver device being effectively connected with said valve housing and a second part of said driver device with said closure bar when said receiving unit is arranged at said valve unit and, in relation to said valve unit is located in the predetermined actuating position.

9. The sampling device according to claim 8, wherein said second part of said driver device effectively connected with said closure bar is a recess and said first part of said driver device effectively connected with said valve housing includes a cam that can be inserted into the recess.

10. The sampling device according to claim 9, wherein said locking device comprises two parts with a groove arranged at the closure housing and a cam arranged at the valve housing, which may not be inserted into the groove until said receiving unit has been brought to the predetermined actuating position in relation to said valve unit.

11. The sampling device according to claim 8, wherein said locking device includes means, part of which are arranged at said valve housing and another part of which are arranged at said closure housing, and in that said second part of said driver device effectively connected with said valve housing includes said means of said locking device arranged at said valve housing, wherein a first instance, said part of said driver device effectively connected with said closure bar is a recess, and in a second instance, said second part of said driver device effectively connected with said closure housing includes a lever attached at said closure housing and having a cam that can be inserted into the recess.

12. The sampling device according to claim 6, wherein said valve rest together with said discharge bore hole and said discharge opening form a unit sealed in relation to said valve housing where it is fastened in a removable way.

* * * * *